(12) United States Patent
Moroni et al.

(10) Patent No.: US 6,524,617 B1
(45) Date of Patent: Feb. 25, 2003

(54) SYNERGISTIC FILLER COMPOSITION

(75) Inventors: Antonio Moroni, Morris Plains, NJ (US); Nadhamuni G. Nerella, Bridgewater, NJ (US); Gregory Du Browny, Garfield, NJ (US)

(73) Assignee: ISP Investments Inc., Wilmington, DE (US)

( * ) Notice: Subject to any disclaimer, the term of this patent is extended or adjusted under 35 U.S.C. 154(b) by 0 days.

(21) Appl. No.: 09/915,057

(22) Filed: Jul. 25, 2001

(51) Int. Cl.[7] ................................................. A61K 9/20
(52) U.S. Cl. .................... 424/465; 424/464; 514/772.3; 514/781
(58) Field of Search ................................ 424/464, 465, 424/489

(56) References Cited

U.S. PATENT DOCUMENTS 4,434,152 A  *  2/1984  Horvath et al. ............. 424/465
5,912,013 A  *  6/1999  Rudnic et al. .............. 424/465

* cited by examiner

*Primary Examiner*—James M. Spear
(74) *Attorney, Agent, or Firm*—Walter Katz; William J. Davis; Marilyn J. Maue

(57) ABSTRACT

A synergistic filler composition for making pharmaceutical tablets of sufficient tablet hardness at low compression force, and low friability, to preclude damage to the tablet upon further processing, and without requiring a substantial increase in the size of the tablet, comprising (a) a PVP-VA copolymer and (b) a microcrystalline cellulose.

2 Claims, 4 Drawing Sheets

Hardness of compacted PVP/VA mixes with silicified MCC.

Hardness of compacted PVP/VA mixes with MCC 102.

Compression Profile of 67% APAP tablets made with silicified MCC and with/without PVP/VA copolymer.

—◇— Sil. MCC 25%+ PVP/VA 5%
—□— Sil. MCC 30%

Compression Profile of APAP 67% tablets made with MCC 102 and with/without PVP/VA copolymer.

—◇— MCC 102 25%+ PVP/VA 5%
—□— MCC 102 30%

Compression Profile of 60% ASA tablets made with silicified MCC and with/without PVP/VA copolymer.

—◇— Sil. MCC 27%+ PVP/VA 10%
—□— Sil MCC 37%

Compression Profile of ASA 60% tablets made with MCC 102 and with/without PVP/VA copolymer.

—◇— MCC 102 27%+ PVP/VA 10%
—□— MCC 102 37%

Compression Profile of Diltiazem HCl 67% tablets made with MCC 102 and with/without PVP/VA copolymer.

SYNERGISTIC FILLER COMPOSITION

BACKGROUND OF THE INVENTION

1. Field of the Invention

This invention relates to pharmaceutical tableting, and, more particularly, to a synergistic filler composition which provides increased tablet hardness and low friability at low compression forces without increasing the size of the tablet.

2. Description of the Prior Art

Many commercial filler materials are used including microcrystalline cellulose and silicified microcrystalline cellulose inn the manufacture of pharmaceutical tablets. Such materials are described in the paper by Tobyn, M. J. in Int. J. of Pharmaceutics, 169, 183–194 (1998). However drugs which are difficult to compress require tableting machines which can operate at high compression forces in order to provide suitable hardness and low friability properties. Also, large amounts of the filler may be necessary to achieve these results, which, disadvantageously, increases the size of the tablet.

Accordingly, it is an object of this invention to provide a drug tableting filler composition of two components which act synergistically with respect to increasing hardness and decreasing friability for pharmaceutical tablets at a given compression force, and without increasing the size of the tablet.

This and other objects and features of the invention will be made apparent from the following description of the invention

SUMMARY OF THE INVENTION

Figure 1:
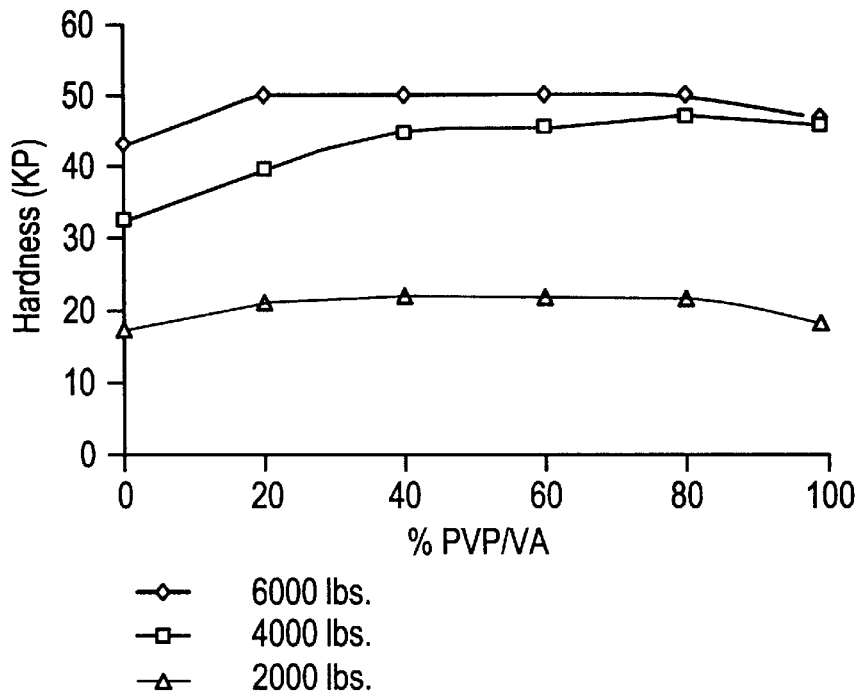
FIG. 1 is a plot of tablet hardness (KP) vs. concentration (wt. %) of PVP-VA copolymer in a composition with silicified microcrystalline cellulose (silicified MCC/ProSolv®) at a given compression force.

What is described herein is a synergistic filler composition for making pharmaceutical tablets of increased tablet hardness and low friability without substantially increasing the size of the tablet, comprising (a) a PVP-VA copolymer and (b) microcrystalline cellulose.

Preferred compositions are those wherein (b) is a silicified microcrystalline cellulose; and (a) is present in an amount of about 5–30%; most preferably 10–20%.

Other preferred compositions are those wherein (a) comprises, by weight, 80–60% PVP and 20–40% VA.

DETAILED DESCRIPTION OF THE INVENTION

In this invention, there is provided synergistic filler compositions of (a) vinyl pyrrolidone-vinyl acetate copolymers, and (b) microcrystalline cellulose, preferably silicified microcrystalline cellulose, which provide a synergistic increase in hardness, and a synergistic decrease in friability, for tableted drugs containing such fillers. These results are achieved herein with only a minimum amount of the filler composition, and without increasing the size of the tablet.

The invention will be further described by reference to the experimental results illustrated in the drawings.

Figure 2:
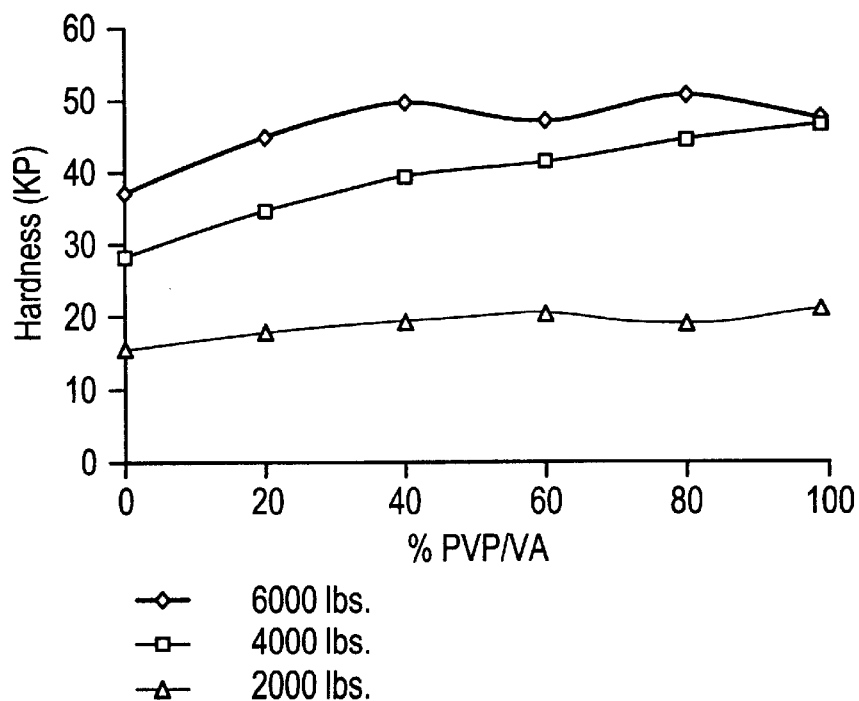
FIG. 2 is a similar plot for mixtures of copolymer and microcrystalline cellulose (MCC 102).

Accordingly, FIGS. 1 and 2 shows a plot of tablet hardness (KP) vs. concentration (wt. %) of PVP-VA copolymer in a composition with microcrystalline cellulose at a given compression force of 2000, 4000 and 6000 lbs. As shown in FIGS. 1 and 2, the composition of the invention provides a synergistic increase in tablet compressibility (hardness) with an increase in the concentration of PVP-VA copolymer in the composition up to about 30 wt. % of PVP/VA copolymer, as evidenced by the convex shape of the curve. The maximum synergistic effect is obtained at about 20 wt. % PVP-VA copolymer. Further increases in copolymer produces only marginal improvement in tablet hardness.

These results contrast with the individual components alone, or PVP-VA copolymer with other known fillers, such as lactose or dicalcium phosphate, where the hardness increase is observed to be only linear with increasing copolymer concentration.

The microcrystalline cellulose component of the composition is available commercially as ProSolv® (silicified microcrystalline cellulose) and as MCC 102 (microcrystalline cellulose).

The advantageous results demonstrated herein for the composition of the invention were obtained similarly for drugs which are difficult to compress into small tablets without using an excessive amount of filler/binder. Such large amounts of filler/binder would preclude formulation of the drug into tablets of high dosage.

Figure 3:
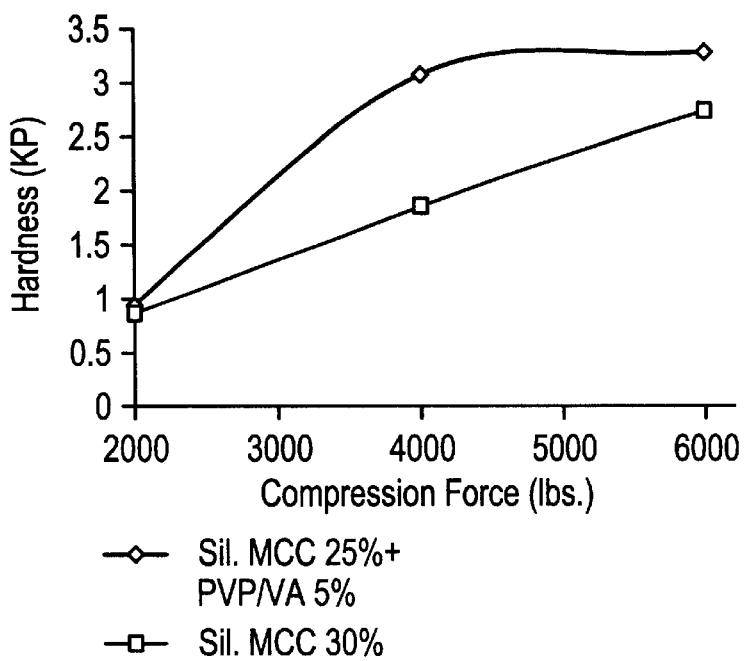
FIG. 3 is a similar plot for a drug tablet of 67 wt. % acetaminophen (APAP) and silicified microcrystalline cellulose, with and without PVP/VA copolymer.
Figure 4:
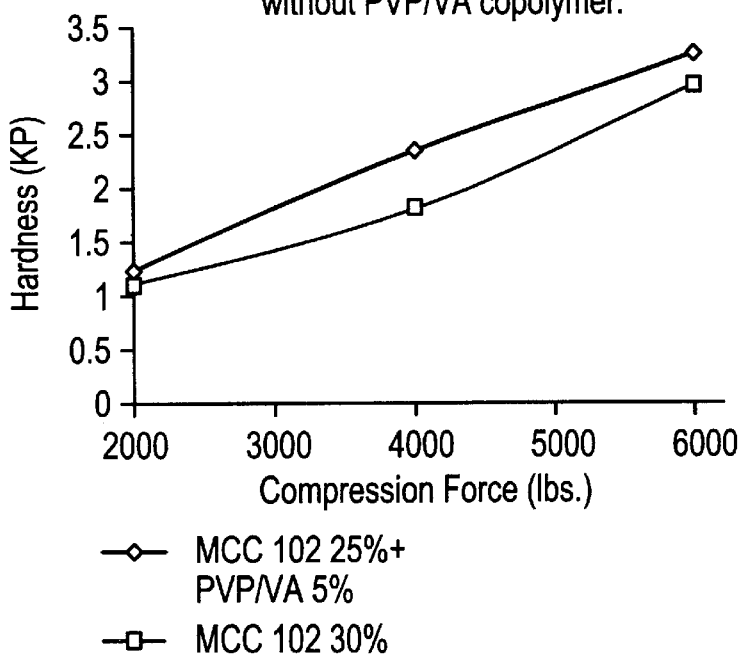
FIG. 4 is a similar plot as FIG. 3 for a composition containing microcrystalline cellulose.

Referring now to FIGS. 3 and 4, there is shown the manufacture of drug-containing tablets with the composition of the invention using acetaminophen as a model drug.

COMPOSITIONS OF DRUG TABLETS (WT. %)

FIGS. 3–4

67 APAP
30 Copolymer (25 cellulose+5 PVP/VA)
2 PVPP (XL)
0.5 SiO$_2$ (colloid)
0.5 Mg stearate
100

FIGS. 5–6

60 Aspirin
37 Copolymer (27+10)
2 PVPP (XL)
0.5 SiO$_2$
0.5 Mg stearate
100

FIG. 7

65 Diltiazem HCl
32 Copolymer (22+10)
2 PVPP (XL)
0.5 SiO$_2$
0.5 Mg stearate
100

Figure 5:
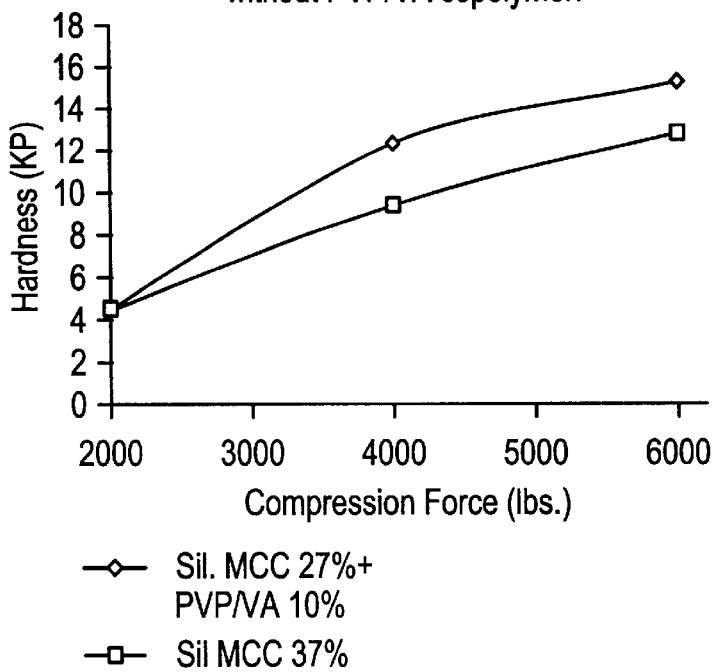
FIG. 5 is a similar plot of 60% aspirin and silicified microcellulose with and without PVP/VA copolymer.
Figure 6:
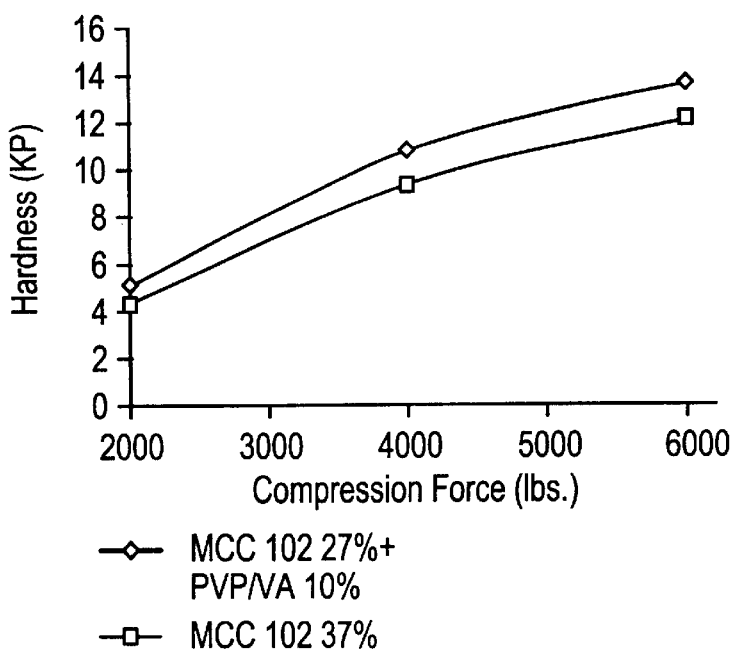
FIG. 6 is a similar plot of a drug tablet with 60 wt. % aspirin and a mix of microcrystalline cellulose (MCC 102) with and without PVP/VA copolymer.
Figure 7:
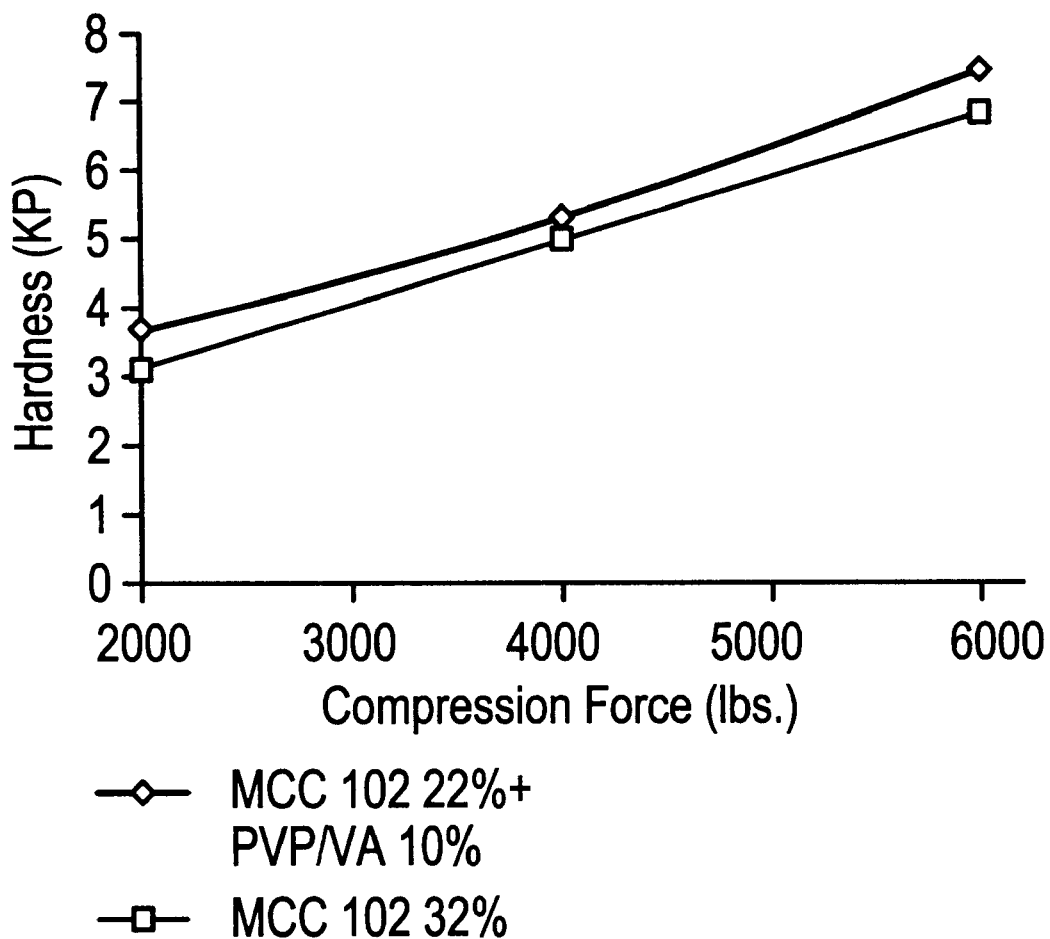
FIG. 7 is a similar plot as FIG. 6 of a drug tablet with 67 wt. % diltiazem HCl as the model drug.

Similar synergistic effects were obtained for aspirin tablets containing (FIGS. 5 and 6) and for diltiazem HCl (FIG. 7) as model drugs.

In summary, the invention composition herein provides a synergistic action in drug tableting formulations of even difficult to compress drugs. The observed hardness is sufficient to prevent damage to the tablet upon further processing of the tablet, including coating and packaging. The tablet hardness obtained herein is preferably at least 3 KP, and its friability is <0.7%, usually <0.5%. Both properties are indicative of a new and improved composition in the field of drug tableting.

While the invention has been described with particular reference to certain embodiments thereof, it will be understood that changes and modifications may be made which are within the skill of the art. Accordingly, it is intended to be bound only by the following claims, in which:

What is claimed is:

1. A pharmaceutical tablet having a tablet hardness of at least 3 KP at a compression force of 2000–5000 lbs, and a friability of <0.7, comprising a drug ordinarily difficult to compress into tablets, and a synergistic filler composition for making such pharmaceutical tablets without requiring a substantial increase in the size of the tablet, consisting essentially of (a) 5–30% by wt. of a PVP-VA copolymer having a composition of 80–60 wt. % PVP and 20–40 wt. % VA, and (b) a microcrystalline silicified cellulose.

2. A composition according to claim 1 wherein (a) is present in an amount of about 10–20% by wt.

* * * * *